United States Patent [19]
Rudko et al.

[11] Patent Number: 5,830,210
[45] Date of Patent: Nov. 3, 1998

[54] CATHETER NAVIGATION APPARATUS

[75] Inventors: Robert I. Rudko, Holliston; Charles Christopher Negus; Stephen J. Linhares, both of Taunton; Eileen A. Woodruff, Millis, all of Mass.

[73] Assignee: PLC Medical Systems, Inc., Franklin, Mass.

[21] Appl. No.: 734,135

[22] Filed: Oct. 21, 1996

[51] Int. Cl.$^6$ ................................................. A61B 17/36
[52] U.S. Cl. .............................. 606/15; 607/99; 607/89; 607/122; 128/642; 606/41
[58] Field of Search .................... 607/89, 98, 99, 607/100, 113, 116, 122; 606/15, 41; 128/642

[56] References Cited

U.S. PATENT DOCUMENTS

| | | | |
|---|---|---|---|
| 5,026,367 | 6/1991 | Leckrone et al. | 607/89 |
| 5,345,936 | 9/1994 | Pomeranz et al. | 607/122 |
| 5,380,316 | 1/1995 | Aita et al. | 606/15 |
| 5,409,000 | 4/1995 | Imran | 607/122 |
| 5,411,025 | 5/1995 | Webster, Jr. | 607/122 |
| 5,465,717 | 11/1995 | Imran et al. | 607/122 |
| 5,558,073 | 9/1996 | Pomeranz et al. | 607/122 |
| 5,593,405 | 1/1997 | Osypka | 606/15 |

*Primary Examiner*—William E. Kamm
*Assistant Examiner*—Kennedy J. Schaetzle
*Attorney, Agent, or Firm*—Iandiorio & Teska

[57] ABSTRACT

A catheter navigation apparatus includes a catheter system for percutaneous insertion into an internal organ cavity. The catheter system includes a treatment catheter and a navigation catheter; the navigation catheter includes a deployable framework at its distal end; the treatment catheter includes at least one conduit extending from its proximal to its distal end; the conduit having its distal end engaged with the framework; the navigation catheter includes a flexible link interconnecting the framework with a control mechanism at the proximal end of the navigation catheter for driving the link to deploy and retract the framework to guide the distal tip of the treatment catheter to target one or more selected positions on the inner wall of the organ cavity.

13 Claims, 5 Drawing Sheets

CATHETER NAVIGATION APPARATUS

FIELD OF INVENTION

This invention relates to a catheter navigation system apparatus for guiding the targeting of a treatment catheter to one or more sites on the inner wall of an internal organ cavity such as the ventricle of a heart.

BACKGROUND OF INVENTION

Transmyocardial revascularization (TMR) is a surgical treatment for cardiovascular disease. Present TMR procedure is an open chest technique which uses a laser beam to drill holes in the myocardium, specifically the left ventricle. These holes or channels extend through the entire thickness from the outside surface through to the ventricle. The channels heal on the outside but remain open on the inside allowing blood to enter the heart wall tissue from the ventricle.

In another approach TMR could be performed percutaneously (endocardial revascularization) using a catheter introduced intravenously so that the tip of the catheter is inside the left ventricle where the holes or channels can be created from the inside toward but not through the outside. The energy used to drill these endocardial channels can be mechanical, e.g., a needle, a scissor; electrical, e.g., bipolar or unipolar electric current, r.f., microwave; or optical, e.g., laser. In one combined mechanical approach a holmium laser initiates the channel and a force is applied through the tip of the catheter to deepen the channel. One problem in percutaneous TMR procedures is that, unlike in open chest TMR, channels being drilled are not plainly visible but their positions must be controlled to prevent the channels being drilled too close or too far from one another or in undesirable areas. Monitoring of their locations can be done with biplanar fluoroscopy but this is expensive and can be confusing even to experienced physicians under the stress of performing heart surgery. This approach is not truly reliable, is expensive, and requires additional equipment in the operating theater.

Historically, catheters delivering energy (optical, electrical, or mechanical) were developed for clearing blockages in a vessel lumen where the distal tip of the catheter is imaged while inside the vessel lumen and easily viewed to reference the position of the catheter to the treatment site within the vessel. The vessel guides the catheter to the treatment site and constrains its motion lateral to the vessel. But this control is not available in endocardial revascularization or other protocols administering to cavities in internal organs, which requires making a blind hole.

SUMMARY OF INVENTION

It is therefore an object of this invention to provide a catheter navigation apparatus for guiding treatment catheter procedures.

It is a further object of this invention to provide such a catheter navigation apparatus which makes it easier to guide a treatment catheter to a treatment site.

It is a further object of this invention to provide such a catheter navigation apparatus which makes it easier to keep the treatment catheter targeted to a selected site during treatment.

It is a further object of this invention to provide such a catheter navigation apparatus for guiding the treatment catheter in percutaneous transmyocardial revascularization surgery.

It is a further object of this invention to provide such a catheter navigation apparatus which is reliable, inexpensive, requires virtually no additional equipment space and is easy to interpret.

It is a further object of this invention to provide such a catheter navigation apparatus which is accurate and consistent.

The invention results from the realization that a truly safe, reliable and inexpensive catheter navigation apparatus for guiding the position of the administering catheter in percutaneous transmyocardial revascularization surgery or other protocols on internal organ cavities which does not require extensive equipment within the surgical suite or special expertise can be effected by attaching to a navigation catheter, having a deployable framework for deployment and rotation inside the cavity of an organ, the distal end of a treatment catheter so that the treatment catheter can be guided to and kept aimed at one or more targeted treatment sites.

This invention features a catheter navigation apparatus including a catheter system for percutaneous insertion into an internal organ cavity. The catheter system includes a treatment catheter and a navigation catheter. The navigation catheter includes a deployable framework at its distal end. The treatment catheter includes at least one conduit extending from its proximal to its distal end. The conduit has its distal end engaged with the framework. The navigation catheter includes a flexible link interconnecting the framework with a control mechanism at the proximal end of the navigation catheter for driving the link to deploy and retract the framework to guide the distal tip of the treatment catheter to target one or more selected positions on the inner wall of the organ cavity.

In a preferred embodiment the treatment catheter may include a plurality of conduits fixed to the framework in spaced relationship to one another. The framework may include at least one guide device for removably engaging the distal end of the at least one conduit. The control mechanism may include an actuator device for moving the flexible link generally along its longitudinal axis to deploy and retract the framework and for rotating the flexible link about its longitudinal axis to rotate the deployed framework within the organ cavity. The treatment catheter may include at its proximal end an energy source for introducing tissue ablative energy to the conduit and through the distal end of the conduit to the inner wall of the organ cavity. The navigation catheter may include means to rotate the deployed framework within the cavity of the organ. The energy source may include a laser and the conduit may include a fiber optic element. The conduit may contain control wires for operating a cutting mechanism at its distal end, or the hollow passage may contain electrical conductors for conveying electrical energy to electrodes at the distal end. The framework may include at least three strands or at last two strands spaced apart other than 180°, and may include distinguishing indicia for determining the orientation of the framework.

In a more specific application the invention may encompass a cardiac catheter navigation apparatus for performing percutaneous transmyocardial revascularization, the apparatus including a catheter system for percutaneous insertion into a heart ventricle. The catheter system may include a treatment catheter and a navigation catheter. The navigation catheter may include a deployable framework at its distal end. The treatment catheter may include at least one conduit extending from its proximal to its distal end. An energy source at its proximal end may be used to introduce tissue ablative energy to the conduit and through the distal end of the conduit to the inner wall of the heart ventricle to perform transmyocardial revascularization. The conduit has its distal end engaged with the framework. The navigation catheter includes a flexible link interconnecting the framework with the control mechanism at the proximal end of the navigation catheter for driving the link to deploy and retract the framework to guide the distal tip of the treatment catheter to target one or more selected positions on the inner wall of the heart ventricle to perform transmyocardial revascularization.

In a preferred embodiment the energy source may include a laser and the conduit may include a fiber optic element. The navigation catheter may include means to rotate the deployed framework within the ventricle of the heart.

DISCLOSURE OF PREFERRED EMBODIMENT

Other objects, features and advantages will occur to those skilled in the art from the following description of a preferred embodiment and the accompanying drawings, in which.

Figure 7A:
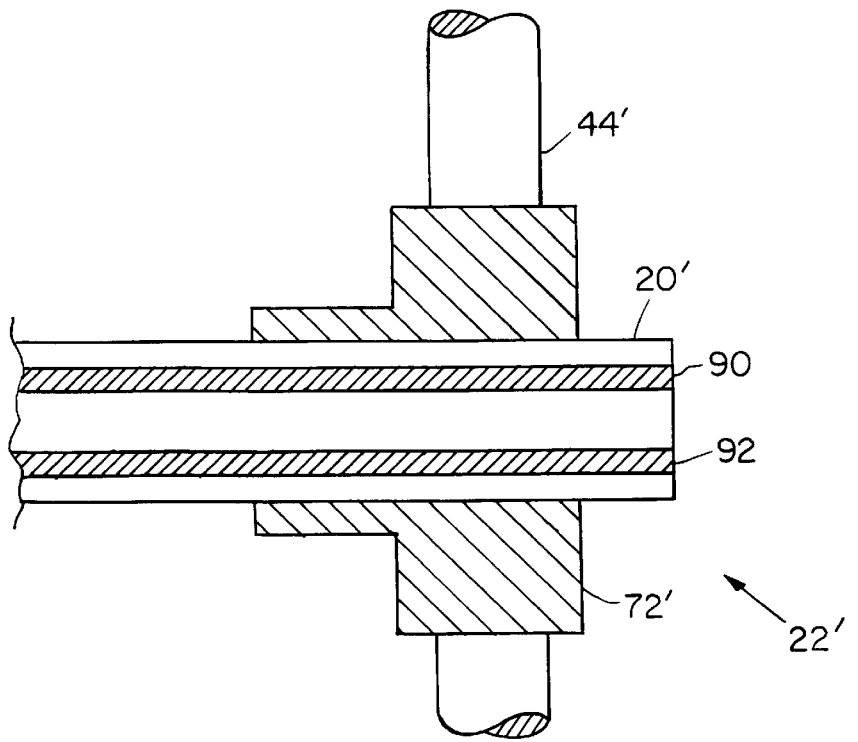
Figure 7B:
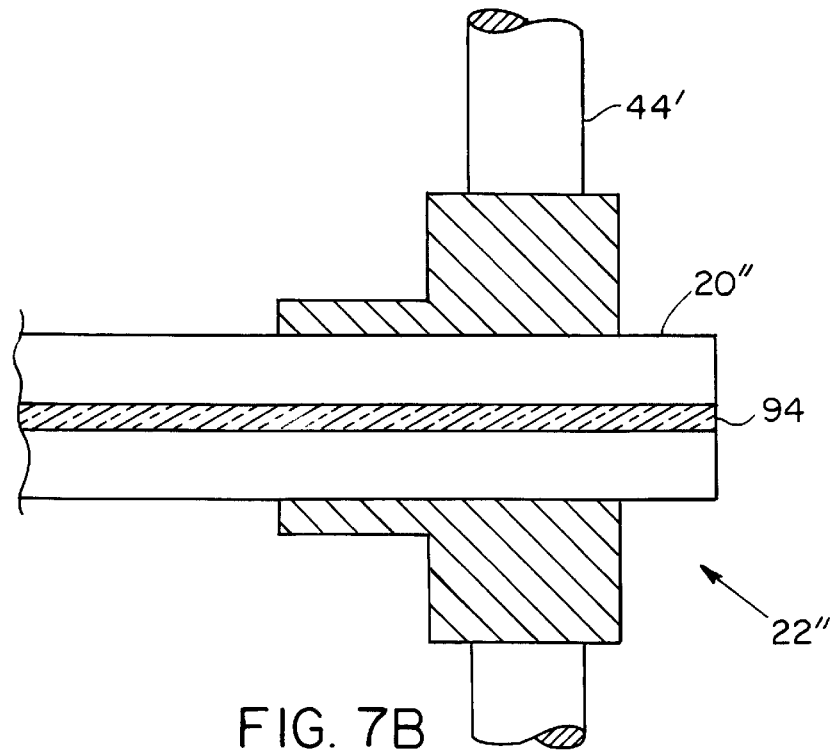
Figure 7C:
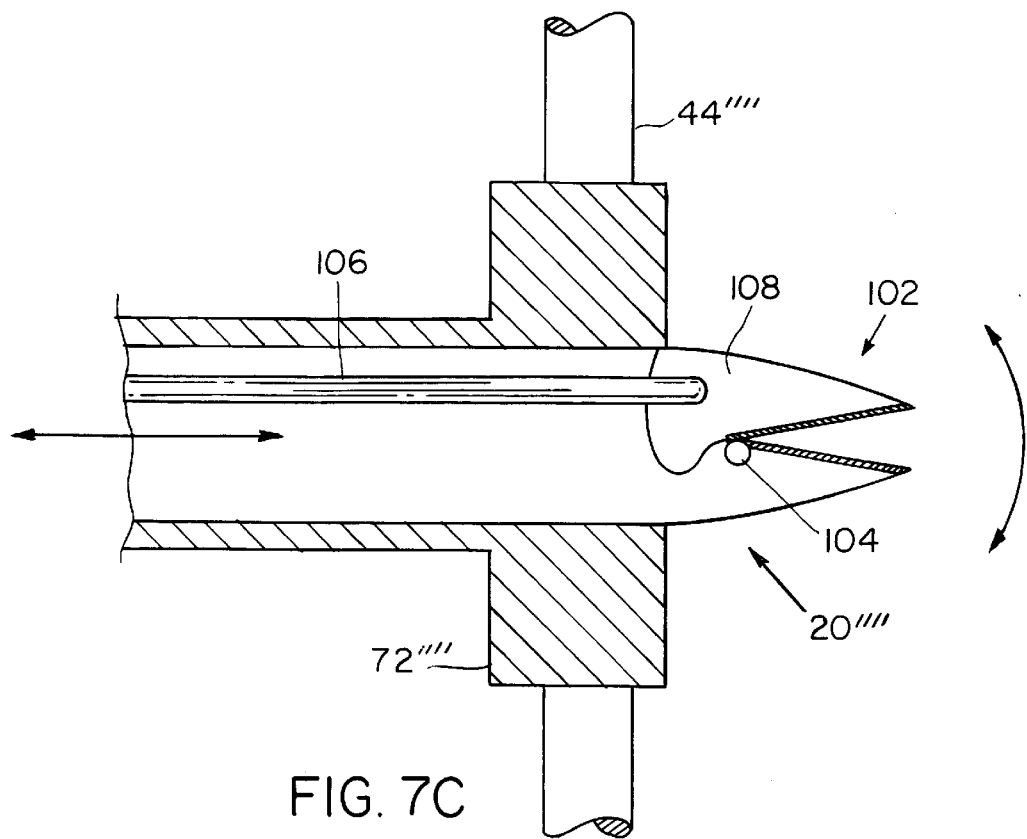

FIGS. 7A–C are enlarged detailed sectional views of the distal end of the treatment catheter showing three different ablative technologies.

Figure 1:
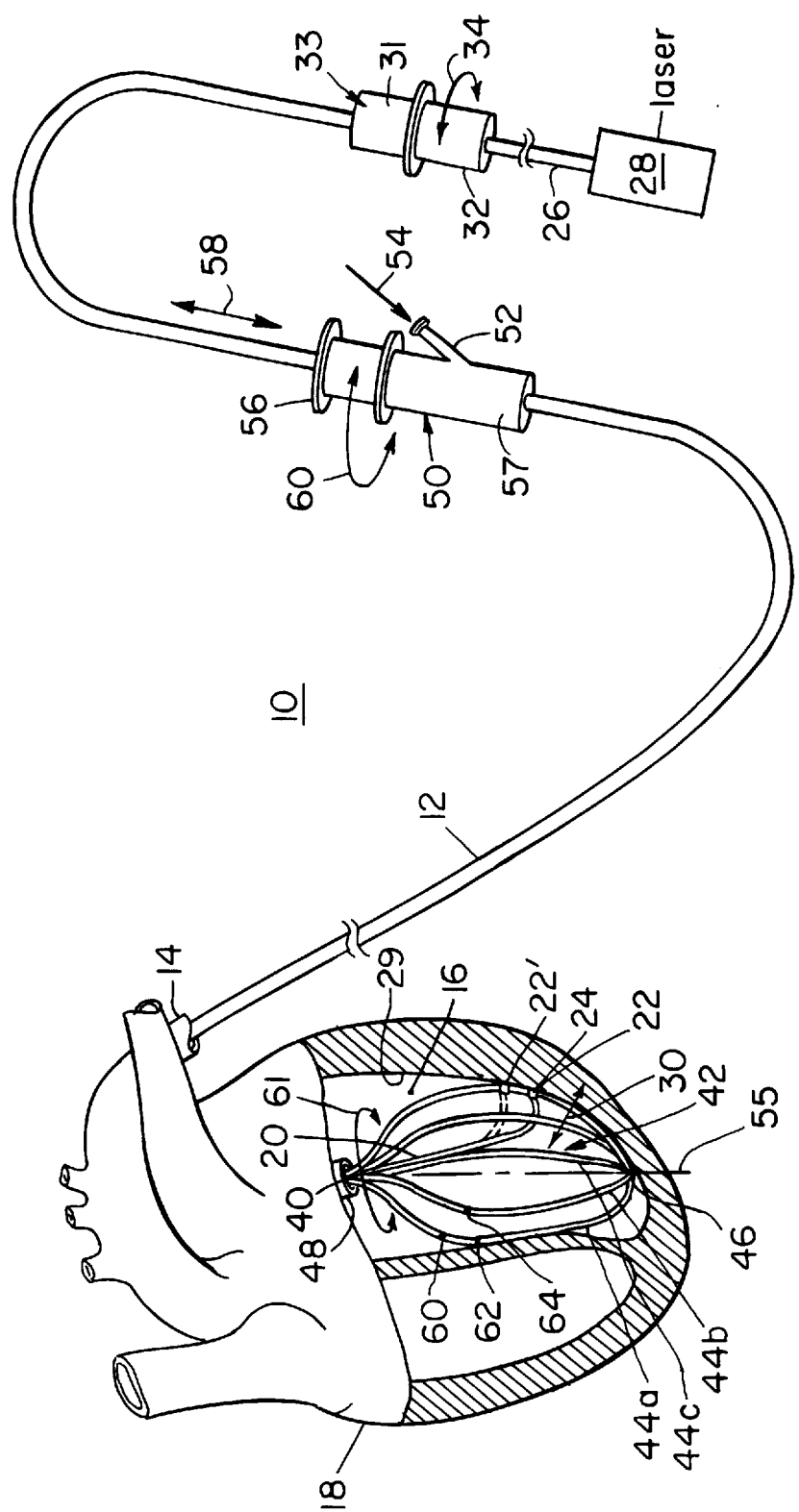
FIG. 1 is a three-dimensional schematic drawing of a catheter navigation apparatus according to this invention with its framework deployed in the left ventricle of a human heart.

There is shown in FIG. 1 a catheter navigation apparatus according to this invention. In this specific embodiment catheter navigation apparatus 10 is constructed as a cardiac catheter navigation apparatus for performing percutaneous transmyocardial revascularization. Apparatus 10 includes a catheter assembly 12 which is threaded through the aorta 14 and into the left ventricle 16 of a human heart 18. Catheter assembly 12 includes two catheters: treatment catheter 20, the distal end 22 of which includes a lens for focusing laser energy delivered through fiber optic element 26 from laser 28. Distal end 22 of treatment catheter 20 may be moved to and fro, that is, toward and away from, heart wall 29 in the direction indicated by arrow 30 by manipulating knob 32 of treatment catheter control 33 to translate it in the direction of arrows 34. Treatment catheter control 33 is constructed and operates in a conventional manner as is well known in the art. Knob 32 is translatable and rotatable with respect to its base 31. Knob 32 is rotated in the direction of arrow 34 in order to curl the distal end 22 of treatment catheter 20 as shown by the dashed lines 22'. The distal end of navigation catheter 40 includes a cagelike framework 42 which in FIG. 1 is in a deployed state in left ventricle 16. Framework 42 includes a plurality of flexible strands 44, at least three, which are joined at their apex 46 at one end and joined at their base to a control wire, not visible in FIG. 1 but visible in FIG. 2. Framework 42 is deployed by extending it beyond the distal end 48 of catheter assembly 12. This is done using navigation catheter control 50.

Figure 6:
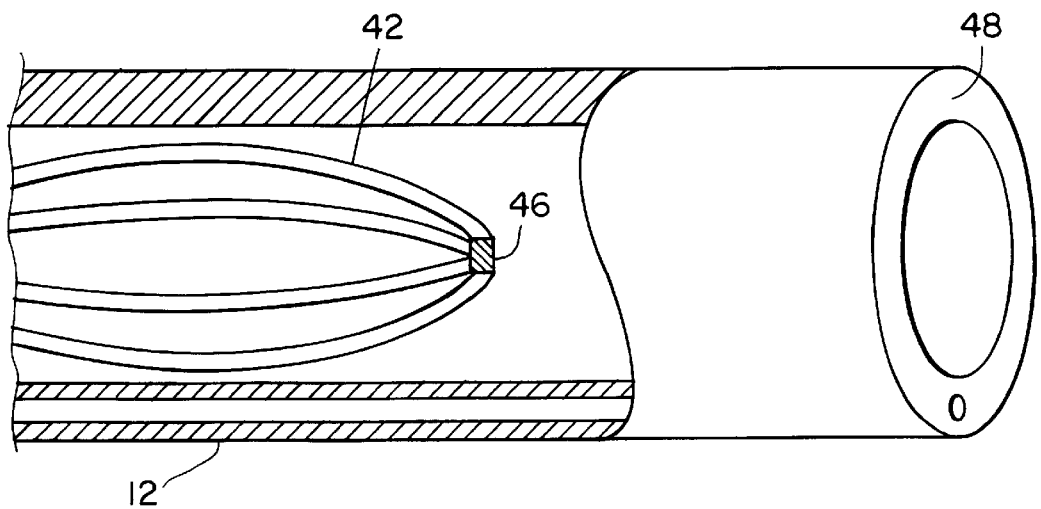
FIG. 6 is a view similar to FIG. 2 but with the framework retracted.

Navigation catheter control 50 includes a port 52 for receiving guide wire 54 which is used to install catheter assembly 12 in the patient's aorta and heart. This is done in the conventional fashion by threading guide wire 54 through the patient's arteries and into the ventricle, as the surgeon manipulates it in the normal way, and then sliding the catheter assembly 12 along the guide wire so that it follows the guide wire through the arteries and into the ventricle. Navigation catheter control 50 also includes control knob 56 which can be translated in and out relative to base 57 along the longitudinal axis 55 of catheter 20 as indicated by arrow 58 to advance and retract framework 42. When framework 42 is advanced it deploys and expands to gently fill ventricle 16. When it is retracted it collapses and withdraws into the end 48 of catheter assembly 12 as can be seen in FIG. 6. When knob 56 is rotated as indicated by arrow 60, framework 42 is rotated, arrow 61, about its longitudinal axis 55 in ventricle 16.

Figure 2:
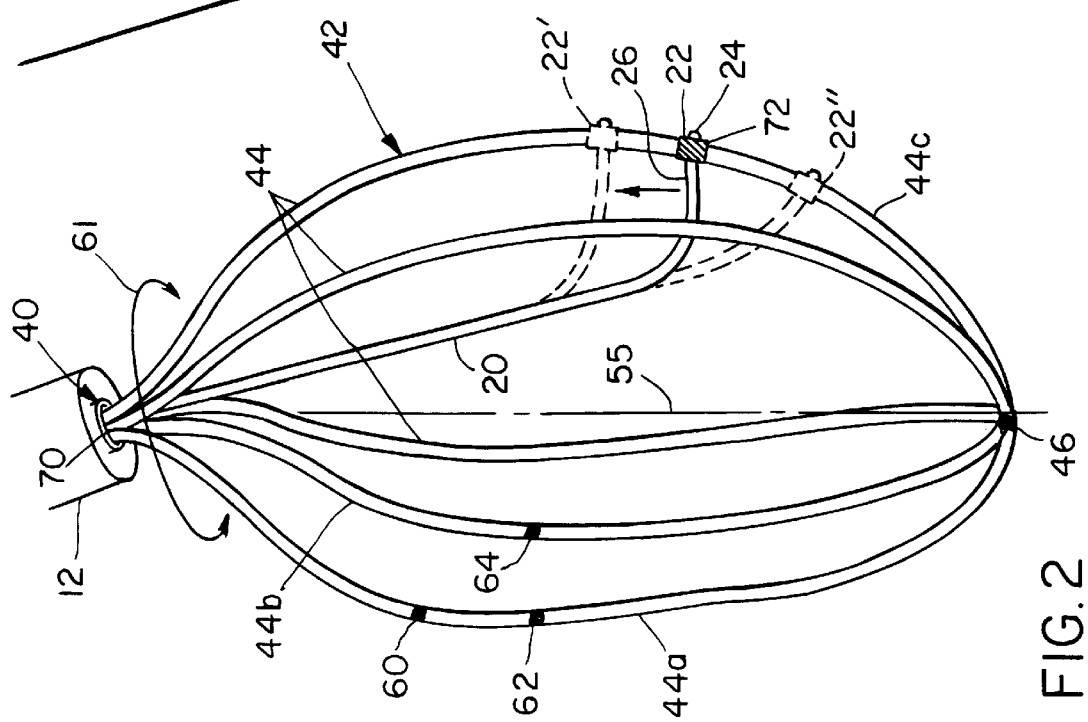
FIG. 2 is an enlarged detail view of the deployed framework of FIG. 1 for guiding the movable distal end of the treatment catheter.

Orientational indicators such as radiopaque, ultrasonically distinct or otherwise distinguishable indicia are provided on framework 42. For example two such indicia 60, 62, FIG. 2, are provided on strand 44*a* and one such indicia 64 on strand 44*b*. So long as these two strands are not 180° opposed they can be used in simple flat fluoroscopy imaging to determine the orientation of framework 42 so that the surgeon with a quick glance at the fluoroscope image can determine the orientation of framework 42 and thus the position of the distal end 22 of treatment catheter 20.

Figure 3:
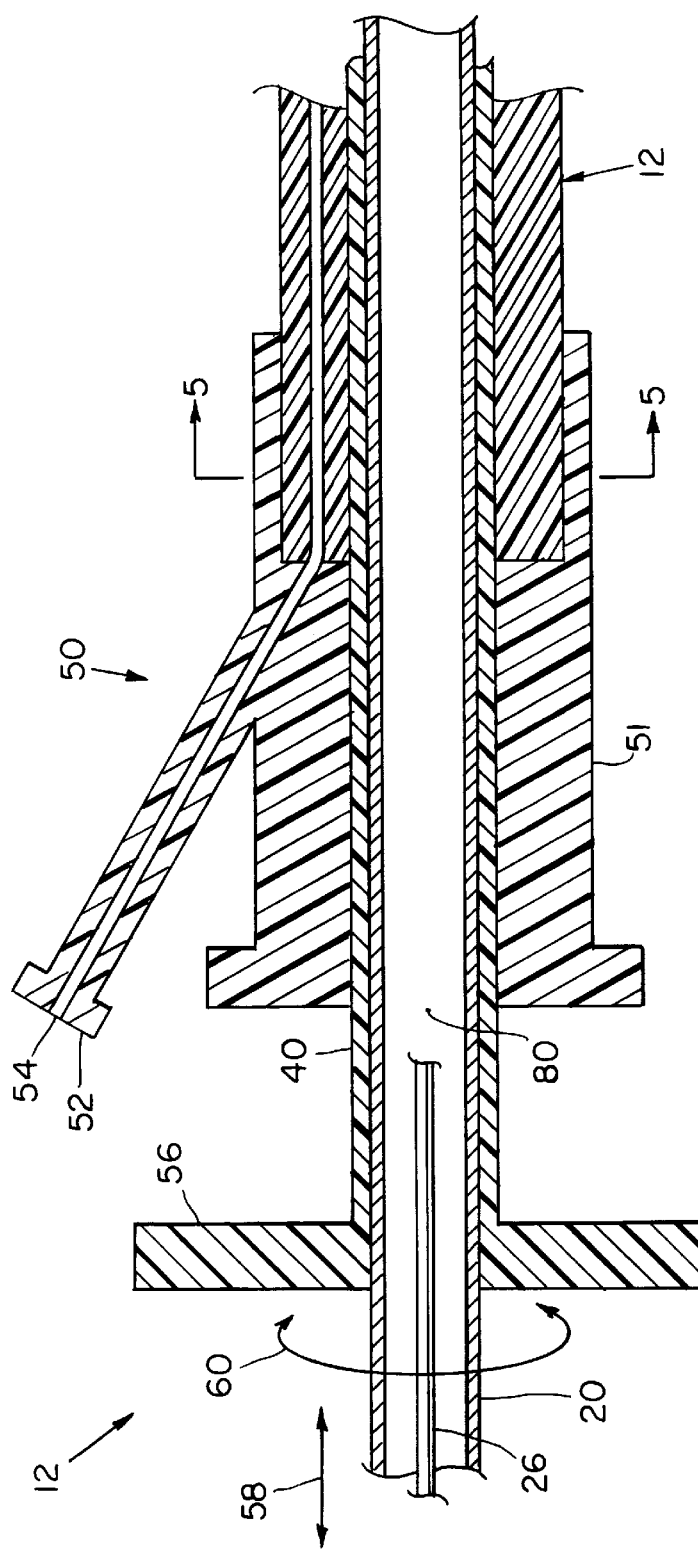
FIG. 3 is an enlarged detail cross-sectional schematic of the navigation catheter control of FIG. 1.

As shown in FIG. 2, treatment catheter 20 and navigation catheter 40 are combined together in lumen 70. When knob 56 is moved to and fro in the direction of arrow 58, FIG. 1, framework 42 is alternately deployed and retracted, respectively. If knob 56 is rotated as indicated by arrow 60, FIG. 1, framework 42 in turn rotates as indicated by arrow 61, FIG. 2. When it is desired to move distal end 22 of fiber optic element 26 of treatment catheter 20, knob 32 is rotated in the direction of arrow 34, FIG. 1, and this causes catheter 20 to uncurl as shown at 22" in FIG. 2, or to curl as shown 15 at position 22', FIG. 1. This causes a guide device, e.g., sliding block 72, to move up and down along strand 44*c*, thereby controlling or guiding distal end 22 and lens 24 so that it applies the ablative laser energy at precisely the point desired by the surgeon. As can be seen more clearly in FIGS. 3 and 4, catheter assembly 12 is fixed to base 51 of navigation catheter control 50 and knob 56 is fixed to navigation catheter 40 so that the motion of knob 56 is directly transmitted through catheter 40 to strands 44. The clearance between the inner surface of base 51 and the outer diameter of navigation catheter 40 is small in order to provide a seal and prevent significant blood loss.

Figure 4:
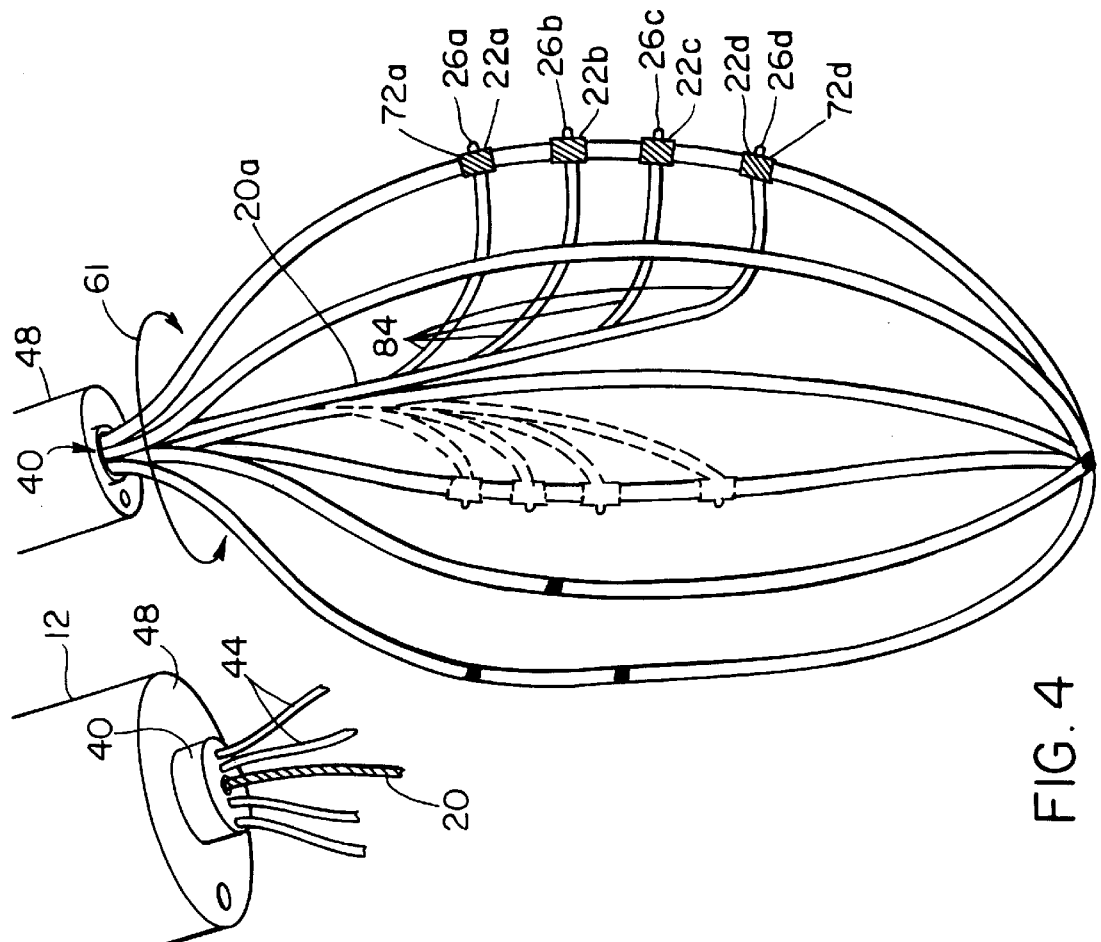
FIG. 4 is a view similar to FIG. 2 with the single movable treatment catheter replaced by a number of fixed treatment catheters.
Figure 5:
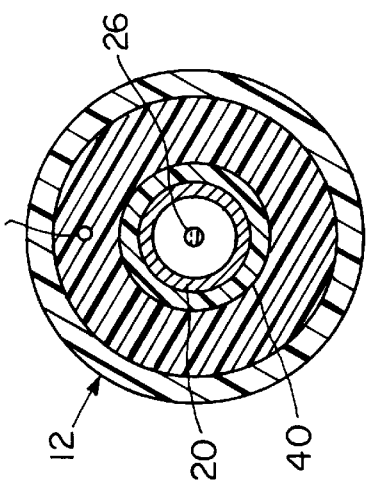
FIG. 5 is a cross-sectional view taken along line 5—5 of FIG. 3.

Treatment catheter 20 may include a hollow center portion which can contain a single strand of fiber optic material 26 as shown, or a multi-stranded optical bundle, or it may contain electrical conductors. Passage 80 may also be used to contain guide wires for operating cutting or snipping mechanisms, as shown in FIG. 7C. Passage 80 may also include a plurality of fiber optic elements 84 to be deployed as shown in FIG. 4 wherein there are a plurality of fiber optic elements 26*a*, 26*b*, 26*c*, 26*d*, contained in treatment catheter 20*a*, each of whose distal end 22*a–d* is fixably attached at block 72*a–d* to their respective strands so that no curling of the distal end is required and the rotational motion of knob 32, FIG. 1, in the direction of arrow 34 is not necessary. Another view of treatment catheter 20 and navigation catheter 40 included in the catheter assembly 12 is shown in cross-section, FIG. 5, where the single fiber optic element 26 can be seen constituting treatment catheter 20 located inside of navigation catheter 40 which in turn is housed in the catheter assembly 12.

Framework 42 is shown in FIG. 6, in the collapsed position before and/or after it occupies the deployed position.

Although thus far the invention has been disclosed as an ablative device which uses laser energy conducted through a fiber optic element to produce the tissue ablation, this is not a necessary limitation of the invention. For example, as shown in FIG. 7A, the distal end of treatment catheter 20' which is supported in mounting block 72' may include a pair of conductors 90, 92 for providing an electric field across the tissue.

Alternatively, as shown in FIG. 7B, treatment catheter 20" may include an optical fiber 94 to provide a laser beam at its distal end 22". In another construction, FIG. 7C, the distal end 22"" of treatment catheter 20"" may include scissors 102 pivoted at 104 with a control wire 106 attached to one of the jaws 108 and threaded back through catheter 20"" to the proximal end where it can be manipulated to operate scissors 10. The invention is also not limited to conventional fiber optic laser delivery as, for example, a side-firing optical fiber could be used.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A catheter navigation apparatus comprising:
   a catheter system for percutaneous insertion into an internal organ cavity; said catheter system including a treatment catheter and a navigation catheter;
   said navigation catheter including a deployable framework at its distal end, said framework having a plurality of flexible strands, said strands expanding to fill the internal cavity when deployed engaging the walls of the cavity in three dimensions;
   said treatment catheter including at least one conduit extending from its proximal to its distal end;
   at least one guide device for movably engaging the distal end of said at least one conduit with said framework;
   said navigation catheter including a flexible link interconnecting said framework with a control mechanism at the proximal end of said navigation catheter for driving said link to deploy and retract said framework to guide the distal tip of said treatment catheter to target one or more selected positions on the inner wall of said organ cavity; and means to rotate said framework within said organ cavity.

2. The catheter navigation apparatus of claim 1 in which said control mechanism includes an actuator device for moving said flexible link generally along its longitudinal axis to deploy and retract said framework and for rotating said flexible link about its longitudinal axis to rotate said framework.

3. The catheter navigation apparatus of claim 1 in which said treatment catheter includes at its proximal end an energy source for introducing tissue ablative energy to said conduit and through the distal end of said conduit to the inner wall of the organ cavity.

4. The catheter navigation apparatus of claim 3 in which said energy source includes a laser and said conduit includes a fiber optic element.

5. The catheter navigation system of claim 1 in which said plurality of flexible strands terminate in a common apex.

6. The catheter navigation system of claim 1 in which said framework rotates through 360°.

7. The catheter navigation apparatus of claim 1 in which said treatment catheter includes a plurality of conduits fixed to said framework in spaced relationship to one another.

8. The catheter navigation apparatus of claim 7 in which said conduit includes a hollow passage for containing control wires for operating a cutting mechanism at its distal end.

9. The catheter navigation apparatus of claim 7 in which said conduit includes an electrical conductor for conveying electrical energy.

10. A cardiac catheter navigation apparatus for performing percutaneous transmyocardial revascularization comprising:
    a catheter system for percutaneous insertion into a heart ventricle; said catheter system including a treatment catheter and a navigation catheter;
    said navigation catheter including a deployable framework at its distal end, said framework having a plurality of flexible strands, said strands expanding to fill the heart ventricle when deployed engaging the walls of the heart ventricle in three dimensions;
    said treatment catheter including at least one conduit extending from its proximal to its distal end; an energy source at its proximal end for introducing tissue ablative energy to said conduit and through the distal end of said conduit to the inner wall of said heart ventricle to perform transmyocardial revascularization;
    at least one guide device for movably engaging the distal end of said at least one conduit with said framework;
    said navigation catheter including a flexible link interconnecting said framework with a control mechanism at the proximal end of said navigation catheter for driving said link to deploy and retract said framework to guide the distal tip of said treatment catheter to target one or more selected positions on the inner wall of said heart ventricle; and means to rotate said framework within said heart ventricle.

11. The catheter navigation apparatus of claim 10 in which said energy source includes a laser and said conduit includes a fiber optic element.

12. The catheter navigation system of claim 10 in which said plurality of flexible strands terminate in a common apex.

13. The catheter navigation system of claim 10 in which said framework rotates through 360°.

* * * * *